US012351612B2

United States Patent
Zhu et al.

(10) Patent No.: US 12,351,612 B2
(45) Date of Patent: Jul. 8, 2025

(54) METHOD FOR PREPARING RECOMBINANT HUMAN NERVE GROWTH FACTOR

(71) Applicant: SUNSHINE GUOJIAN PHARMACEUTICAL (SHANGHAI) CO., LTD., Shanghai (CN)

(72) Inventors: Zhenping Zhu, Shanghai (CN); Haomin Huang, Shanghai (CN); Jianguo Xiao, Shanghai (CN)

(73) Assignee: SUNSHINE GUOJIAN PHARMACEUTICAL (SHANGHAI) CO., LTD., Shanghai (CN)

( * ) Notice: Subject to any disclaimer, the term of this patent is extended or adjusted under 35 U.S.C. 154(b) by 643 days.

(21) Appl. No.: 17/787,558

(22) PCT Filed: Nov. 3, 2020

(86) PCT No.: PCT/CN2020/126147
§ 371 (c)(1),
(2) Date: Jun. 20, 2022

(87) PCT Pub. No.: WO2021/120900
PCT Pub. Date: Jun. 24, 2021

(65) Prior Publication Data
US 2023/0037311 A1  Feb. 9, 2023

(30) Foreign Application Priority Data
Dec. 20, 2019 (CN) .......................... 201911325340.0

(51) Int. Cl.
| | | |
|---|---|---|
| *C07K 14/48* | (2006.01) | |
| *C07K 1/14* | (2006.01) | |
| *C07K 1/20* | (2006.01) | |
| *C07K 1/30* | (2006.01) | |
| *C07K 1/34* | (2006.01) | |
| *C07K 1/36* | (2006.01) | |
| *C12N 15/70* | (2006.01) | |
| *C12P 21/02* | (2006.01) | |

(52) U.S. Cl.
CPC ................ *C07K 14/48* (2013.01); *C07K 1/20* (2013.01); *C07K 1/30* (2013.01); *C07K 1/34* (2013.01); *C07K 1/36* (2013.01); *C12N 15/70* (2013.01); *C12P 21/02* (2013.01)

(58) Field of Classification Search
CPC . C07K 14/48; C07K 1/30; C07K 1/34; C07K 1/36; C07K 1/14; C12N 15/70
See application file for complete search history.

(56) References Cited

FOREIGN PATENT DOCUMENTS

| | | |
|---|---|---|
| CN | 1334271 | 2/2002 |
| CN | 102628058 | 8/2012 |
| CN | 103880943 | 6/2014 |
| CN | 103880944 | 6/2014 |
| CN | 107973848 | 5/2018 |
| WO | 2015097154 A1 | 7/2015 |

*Primary Examiner* — Maryam Monshipouri
(74) *Attorney, Agent, or Firm* — Gregory P. Einhorn; Greer, Burns & Crain, Ltd.

(57) ABSTRACT

Provided is a method for preparing a recombinant human nerve growth factor, which can be used as a therapeutic drug.

12 Claims, 3 Drawing Sheets

Specification includes a Sequence Listing.

SEQUENCE LISTING

```
<160> NUMBER OF SEQ ID NOS: 2

<210> SEQ ID NO 1
<211> LENGTH: 118
<212> TYPE: PRT
<213> ORGANISM: Homo

<400> SEQUENCE: 1

Ser Ser Ser His Pro Ile Phe His Arg Gly Glu Phe Ser Val Cys Asp
1               5                   10                  15

Ser Val Ser Val Trp Val Gly Asp Lys Thr Thr Ala Thr Asp Ile Lys
            20                  25                  30

Gly Lys Glu Val Met Val Leu Gly Glu Val Asn Ile Asn Asn Ser Val
        35                  40                  45

Phe Lys Gln Tyr Phe Phe Glu Thr Lys Cys Arg Asp Pro Asn Pro Val
    50                  55                  60

Asp Ser Gly Cys Arg Gly Ile Asp Ser Lys His Trp Asn Ser Tyr Cys
65                  70                  75                  80

Thr Thr Thr His Thr Phe Val Lys Ala Leu Thr Met Asp Gly Lys Gln
                85                  90                  95

Ala Ala Trp Arg Phe Ile Arg Ile Asp Thr Ala Cys Val Cys Val Leu
            100                 105                 110

Ser Arg Lys Ala Val Arg
        115
```

```
<210> SEQ ID NO 2
<211> LENGTH: 407
<212> TYPE: DNA
<213> ORGANISM: Homo

<400> SEQUENCE: 2
tctagaaata attttgttta actttaagaa ggagatatac catgagtagc agccatccga      60
ttttccatcg cggcgagttt agcgtgtgcg atagcgtgag cgtttgggtg ggcgataaaa     120
ccaccgccac cgacatcaaa ggcaaggaag tgatggtgct gggcgaagtg aatattaata     180
atagcgtgtt taaacagtac ttttttgaaa ccaaatgccg cgatccgaat ccggtggata     240
gcggttgccg cggcattgac agcaagcact ggaacagcta ctgcacaacc acccatacct     300
tcgtgaaagc tttaaccatg gatggcaaac aagctgcttg gcgctttatt cgtatcgata     360
ccgcttgtgt gtgcgtgctg agccgcaaag cagtgcgttg actcgag                   407
```

METHOD FOR PREPARING RECOMBINANT HUMAN NERVE GROWTH FACTOR

RELATED APPLICATIONS

This application is a national phase application claiming benefit of priority under 35 U.S.C. § 371 to International (PCT) Patent Application serial number PCT/CN2020/126147, filed Nov. 3, 2020, which claims benefit of priority to Chinese Patent Application No. CN 201911325340.0, filed Dec. 20, 2019. The aforementioned applications are expressly incorporated herein by reference in their entirety and for all purposes.

FIELD OF THE INVENTION

The present invention belongs to the field of biotechnology, and relates to the preparation of a recombinant human nerve growth factor with high purity, high activity and no modification by genetic engineering.

BACKGROUND OF THE INVENTION

Oxervate (cenegermin, recombinant human nerve growth factor, rhNGF) is an eye drop originally developed by the Italian drugmaker Dompé. It is an orphan drug for the treatment of adult patients with moderate-to-severe neurotrophic keratitis (NK), and is currently marketed in the European Union and the United States. In addition, its indication for the treatment of Alzheimer's disease is also under development.

In order to prepare recombinant human nerve growth factor, the original manufacturer provides a method comprising first expression of proNGF inclusion bodies, followed by denaturation and renaturation, purification of the proNGF renaturation solution, enzyme-digestion and purification to obtain the recombinant human nerve growth factor. However, this method requires enzyme-digestion as well as purification after enzyme-digestion, which has many procedures and a cumbersome process.

Therefore, researchers have been hoping to find a simple, direct denaturation and renaturation method. Collins, et al. (U.S. Pat. No. 5,986,070) provides a method of direct denaturation and renaturation of rhNGF, in which Tris is used as a buffer, denaturation is performed under the condition of 8 M urea, and renaturation is performed under the condition of 8 M urea. The method yields rhNGF with high activity. However, as determined by mass spectrometry, the rhNGF obtained by this method has many impurities whose molecular weights are close to that of rhNGF, and these impurities may be the modified products of rhNGF. Since the modified rhNGF and the unmodified rhNGF have very similar molecular weights and properties, subsequent separation and purification are difficult. It is difficult to separate them by conventional methods, and even if separated, the yield is low.

SUMMARY OF THE INVENTION

In order to overcome the deficiencies of the prior art, the present invention provides a method for preparing recombinant human nerve growth factor with high purity, high activity and no modification. The inventors of the present invention have found in their long-term research on rhNGF that when ammonium bicarbonate ($NH_4HCO_3$) is used as a buffer, and denaturation and renaturation is performed in the presence of urea, non-target protein impurities are greatly reduced, and the recombinant human nerve growth factor prepared according to the present invention has high purity and good biological activity, can be used as a therapeutic drug and has good application prospects.

In order to achieve the above objects, the present invention adopts the following technical solutions:

The invention provides a method for preparing recombinant human nerve growth factor, comprising the following steps:
(a) expressing inclusion bodies of the recombinant human nerve growth factor in *E. coli*, and isolating the inclusion bodies from the *E. coli*;
(b) washing the inclusion bodies with an inclusion body washing solution;
(c) dissolving the inclusion bodies by addition of a denaturing solution;
(d) renaturing the inclusion bodies by addition of a renaturing solution;
(e) purifying to obtain the recombinant human nerve growth factor;
wherein, ammonium bicarbonate is used as a buffer in the step (d).

The inclusion bodies of recombinant human nerve growth factor can be expressed and isolated using commercial or known *E. coli* protein expression systems. According to a preferred embodiment of the present invention, the step (a) comprises the following steps: the amino acid sequence of human nerve growth factor being shown in SEQ ID NO: 1, whole gene synthesis of the human nerve growth factor gene, insertion of the human nerve growth factor gene into a vector, transformation of the vector into the *E. coli*, expression of the human nerve growth factor gene, disruption of the *E. coli* cells, centrifugation, and collection of precipitation. According to a preferred embodiment of the present invention, the vector is pET28a, the *E. coli* is *E. coli* expression strain BL21(DE3) plyss, the expression is IPTG-induced expression, and the disruption is performed by sonication or homogenization, etc.

After isolation of the inclusion bodies of recombinant human nerve growth factor, the inclusion bodies may be washed with an inclusion body washing solution to remove impurities. The inventors of the present application have made various attempts on combinations of washing solutions for the inclusion bodies, to screen washing protocols that are particularly suitable for the inclusion bodies of recombinant human nerve growth factor of the present invention. According to a preferred embodiment of the present invention, the step (b) comprises the following steps: subjecting the precipitation to resuspension in inclusion body washing solution A, sonication, centrifugation, and collection of precipitation, wherein the inclusion body washing solution A comprises 20-100 mM Tris, 50-150 mM NaCl, 1-10 mM EDTA, 0.5-3% Triton X-100, pH 8.0-8.5; subjecting the precipitation to resuspension in inclusion body washing solution B, sonication, centrifugation, and collection of precipitation, wherein the inclusion body washing solution B comprises 20-100 mM Tris, 50-150 mM NaCl, 1-10 mM EDTA, 1-4 M urea, pH 8.0-8.5; and then subjecting the precipitation to resuspension in inclusion body washing solution C, sonication, centrifugation, and collection of precipitation, wherein the inclusion body washing solution C comprises 20-100 mM Tris, 50-150 mM NaCl, 1-10 mM EDTA, pH 8.0-8.5. More preferably, the step (b) comprises the following steps: subjecting the precipitation to resuspension in inclusion body washing solution A, sonication, centrifugation, and collection of precipitation, repeating the washing step once, wherein the inclusion body washing solution A comprises 50 mM Tris, 100 mM NaCl, 5 mM EDTA, 1% Triton X-100, pH 8.5; subjecting the precipitation to resuspension in inclusion body washing solution B, sonication, centrifugation, and collection of precipitation, repeating the washing step once, wherein the inclusion body washing solution B comprises 50 mM Tris, 100 mM NaCl, 5 mM EDTA, 2 M urea, pH 8.5; and then subjecting the precipitation to resuspension in inclusion body washing solution C, sonication, centrifugation, and collection of precipitation, repeating the washing step once, wherein the inclusion body washing solution C comprises 50 mM Tris, 100 mM NaCl, 5 mM EDTA, pH 8.5.

After purifying the inclusion bodies of recombinant human nerve growth factor, denaturation and renaturation of the inclusion bodies are required to obtain the target protein with the correct folding form and biological activity.

According to a preferred embodiment of the present invention, the step (c) comprises the following steps: adding a denaturing solution to the inclusion bodies, the denaturing solution comprising 8 M urea and 15-25 mM citric acid, pH 2.8-3.2, the denaturing solution being added according to a ratio of wet weight (g):volume (mL) 1:20-30 of the inclusion bodies and the denaturing solution, allowing the inclusion bodies to be dissolved, followed by centrifugation to remove the precipitation. According to a preferred embodiment of the present invention, the denaturing solution comprises 8 M urea and 20 mM citric acid, pH 3.0, the denaturing solution being added according to a ratio of wet weight (g):volume (mL) 1:25 of the inclusion bodies and the denaturing solution.

According to a preferred embodiment of the present invention, the step (d) comprises the following steps: to the denaturing solution, adding ¼ volume of 0.8-1.0 M ammonium bicarbonate pH 8.0-9.0 and 8 M urea solution, adding DTT to a final concentration of 5-10 mM, maintaining at 25-37° C. for 30-60 min; then adding oxidized glutathione to a final concentration of 20-40 mM, maintaining at 25-37° C. for 10-15 min; then adding 19 volumes of dilution buffer, the dilution buffer comprising 50-150 mM $Na_2HPO_4$, 5-15 mM ethanolamine, 4.2-4.6 M urea, 14-18% PEG300, pH 8.3-8.5; then adding cysteine to a final concentration of 1-5 mM; then subjecting the mixture to deaeration with argon and renaturation at 4° C. for 1-7 days; subjecting the renaturing solution to ultrafiltration concentration with 3K membrane to a final concentration of rhNGF of 1-2 mg/mL. More preferably, the concentration of ammonium bicarbonate is 1 M, pH is 8.5, the final concentration of DTT is 5 mM, the final concentration of the oxidized glutathione is 20 mM, and the dilution buffer comprises 100 mM $Na_2HPO_4$, 10 mM ethanolamine, 4.6 M urea, 15.8% PEG300, pH 8.3, the final concentration of cysteine is 3 mM.

After denaturation and renaturation of the inclusion bodies, the target protein can be purified using known chromatography systems. According to an embodiment of the present invention, the step (e) comprises the steps of SP purification and C4 reversed-phase chromatography.

Beneficial effects of the present invention:
1. The present method has simple operation and less steps without enzyme digestion, and the obtained product has less impurities and high purity;
2. The present method does not destroy the biological activity of the target protein, and the obtained product can be used as a candidate drug.

The present invention provides a method for preparing recombinant human nerve growth factor, which has less impurities, high purity and good biological activity, can be used as a therapeutic drug, and has good application prospects.

DETAILED DESCRIPTION OF THE INVENTION

The following examples and experimental examples are used to further illustrate the present invention, but do not limit the present invention in any form.

Unless otherwise specified, the raw materials used in the following examples are all commercially available.

Figure 1:
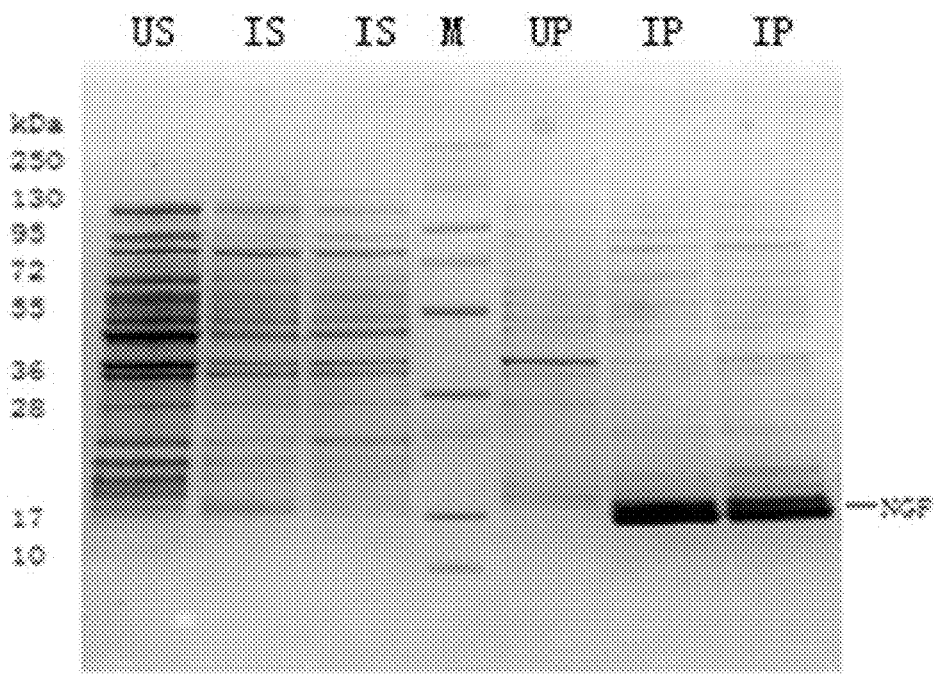
FIG. 1 is the SDS-PAGE pattern of the expression products of the present invention, wherein M represents the protein marker, US and UP represent the supernatant and precipitation of the uninduced expressed strain, respectively, IS and IP represent the supernatant and precipitation of the IPTG-induced expressed strain, respectively.

Example 1: Preparation of rhNGF Inclusion Bodies 1.1 Construction of rhNGF Expression Strain Human mature nerve growth factor (NGF) was allowed to remove the two amino acids at the C-terminus, having the amino acid sequence as shown in SEQ ID NO: 1. The codons were optimized according to the codon preference of *E. coli*, and the whole gene of human nerve growth factor was synthesized, having the gene sequence as shown in SEQ ID NO: 2, inserted into the pET28a multiple cloning sites (MCS) XbaI and XhoI to construct the plasmid hNGFpET28a. The protein was expressed using the strong promoter T7. The plasmid hNGFpET28a was transformed into *E. coli* expression strain BL21(DE3) plyss (purchased from Promega) with 42° C. heat shock, and two colonies were induced by IPTG for expression, disrupted by sonication, and centrifuged at 12,000 rpm for 5 min. The SDS-PAGE pattern of supernatant and precipitation of the expression product is shown in FIG. 1. Bacterial glycerol stock was prepared by adding 15% glycerol to the seed bacteria solution and stored at −80° C.

1.2 IPTG-Induced Expression

Figure 2:
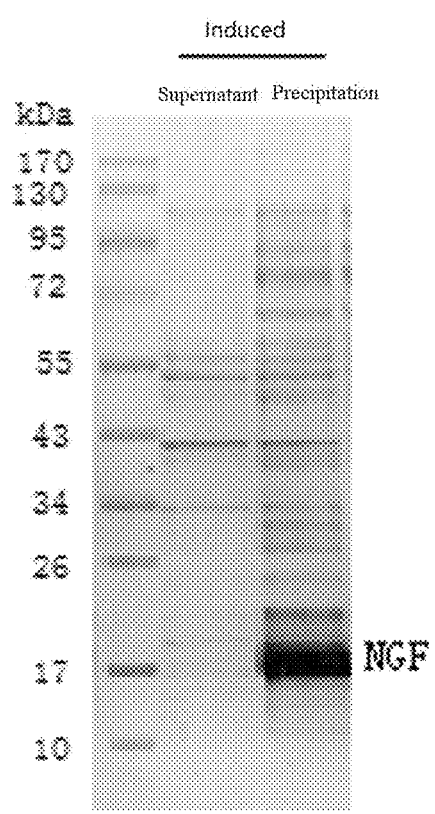
FIG. 2 is the SDS-PAGE pattern of the IPTG-induced expression product of the present invention, wherein M represents the protein marker.

The bacterial glycerol stock was inoculated with a culture medium with an antibiotic in a volume ratio of 1:1000, and cultured at 37° C., 180 rpm overnight; the seed solution was inoculated into the culture medium with an antibiotic in a volume ratio of 1:100, and cultivated at 37° C., 180 rpm until the OD600 was 0.3-0.8; IPTG was added to a final concentration of 1 mM, cultured at 25° C., 170 rpm for another 18 hours; centrifuged at 8500 rpm for 10 min to remove the supernatant and collect the bacteria. Bacterial samples were taken, disrupted by sonication, and the precipitation was detected by SDS-PAGE. The SDS-PAGE pattern of the induced expression products is shown in FIG. 2.

1.3 Isolation of the Inclusion Bodies

Lysis solution (2 mM Tris, 100 mM NaCl, 5 mM EDTA, pH 8.5) was added according to a ratio of wet weight (g):volume (mL) 1:5-1:10 of the bacteria and the lysis solution, sonicated with a 2 sec on and 3 sec off pulse and 80% power for 5 min. The sonication step was repeated four times, and the precipitation was collected by centrifugation at 12,000 rpm, 4° C. for 15 min.

1.4 Purification of the Inclusion Bodies

The inclusion bodies were resuspended in inclusion body washing solution A (50 mM Tris, 100 mM NaCl, 5 mM EDTA, 1% Triton X-100, pH 8.5), sonicated with a 2 sec on and 3 sec off pulse and 80% power for 5 min. The sonication step was repeated once, and the precipitation was collected by centrifugation at 12,000 rpm, 4° C. for 15 min. The washing step was repeated once.

The precipitation was resuspended in the inclusion body washing solution B (50 mM Tris, 100 mM NaCl, 5 mM EDTA, 2 M urea, pH 8.5), sonicated with a 2 sec on and 3 sec off pulse and 80% power for 5 min. The sonication step was repeated once, and the precipitation was collected by centrifugation at 12,000 rpm, 4° C. for 15 min. The washing step was repeated once.

Next, the precipitation was resuspended in the inclusion body washing solution C (50 mM Tris, 100 mM NaCl, 5 mM EDTA, pH 8.5), sonicated with a 2 sec on and 3 sec off pulse and 80% power for 5 min. The sonication step was repeated once, and the precipitation was collected by centrifugation at 12,000 rpm, 4° C. for 15 min.

Example 2: Denaturation, Renaturation and Purification of the rhNGF Inclusion Bodies Using Ammonium Bicarbonate Buffer 2.1 Denaturation of the Inclusion Bodies Denaturing solution (8 M urea, 20 mM citric acid, pH 3.0) was added according to a ratio of wet weight (g):volume (mL) 1:25 of the inclusion body precipitation of Example 1 and the denaturing solution to dissolve the inclusion bodies, and then centrifuged to remove the precipitation.

2.2 Renaturation of the Inclusion Bodies

To the denaturing solution, ¼ volume of 1.0 M ammonium bicarbonate pH 8.5 and 8 M urea solution was added, dithiothreitol (DTT) was added to a final concentration of 5 mM, maintaining at 25° C. for 30-60 min; then oxidized glutathione was added to a final concentration of 20 mM, maintaining at 25° C. for 10-15 min; then 19 volumes of dilution buffer (100 mM $Na_2HPO_4$, 10 mM ethanolamine, 4.6 M urea, 15.8% PEG300, pH 8.3) was added; then cysteine was added to a final concentration of 3 mM; subjecting the mixture to deaeration with argon and renaturation at 4° C. for 1-7 days; subjecting the renaturing solution to ultrafiltration concentration through a 3K membrane to a final concentration of rhNGF of 1-2 mg/mL.

Meanwhile, control samples were provided. The conditions were the same except that ¼ volume of 1 M Tris pH 8.5 and 8 M urea was added to the denaturing solution.

2.3 Purification 2.3.1 SP Purification

SP column: SP XL 1 mL GE company
Sample loading: buffer composition 20 mM NaAc pH 5.0, conductivity 4.5
Elution conditions: gradient elution
A: 20 mM NaAc pH 5.0
B: 20 mM NaAc 2 M NaCl pH 5.0
A to B 20 min.

2.3.2 C4 Reversed-Phase Chromatography

Before the sample loading, the protein was concentrated by ultrafiltration through a 3K membrane to a final concentration of rhNGF of 0.8-1.2 mg/mL.

C4 column: Vydac 214 TP 10 μm C4 250×10 mm
A: 0.1% trifluoroacetic acid $H_2O$ solution
B: 0.1% trifluoroacetic acid acetonitrile solution
Chromatography conditions: flow rate 5 mL/min

| Time (min) | % B |
| --- | --- |
| 0 | 5% |
| 5-10 | 5-20% |
| 10-40 | 20-50% |
| 40-50 | 50-80% |

2.4 Mass Spectrometry Detection

The mass spectrometry conditions are as follows:
UPLC-XEVO G2 Q-TOF LC/MS system from Waters company. Liquid phase configuration of the system: BSM binary high pressure mixing pump, SM sample manager, TUV ultraviolet detector; mass spectrometry configuration of the system: ESI source, Q-TOF detector. Data processing and analysis were performed using Masslynx V4.1 and BiopharmaLynx analysis software (Version: 1.2).

Liquid phase conditions
Chromatographic column: Mass PREP™ Micro Desalting Column 2.1×5 mm (intact protein molecular weight analysis), column temperature: 80° C.;
Mobile phase A: 0.1% FA-$H_2O$
Mobile phase B: 0.1% FA-CAN
Seal Wash solution: 10% IPA
Mass spectrometer cleaning solution: 50% ACN
Mass spectrometer IntelliStart valve cleaning solution: 50% MeOH
Injection volume: 10 μL
Sample chamber temperature: 10° C.
Gradient elution conditions:

|  |  | Time (min) | Flow rate (mL/min) | % A | % B | Curve |
| --- | --- | --- | --- | --- | --- | --- |
| Intact protein molecular weight analysis | Online desalting column | Initial | 0.5 | 95 | 5 | Initial |
|  |  | 0.5 | 0.5 | 95 | 5 | 6 |
|  |  | 0.51 | 0.2 | 95 | 5 | 6 |
|  |  | 2 | 0.2 | 10 | 90 | 6 |
|  |  | 2.1 | 0.5 | 95 | 5 | 6 |
|  |  | 2.7 | 0.5 | 10 | 90 | 6 |
|  |  | 2.8 | 0.5 | 95 | 5 | 6 |
|  |  | 3.4 | 0.5 | 10 | 90 | 6 |
|  |  | 3.5 | 0.5 | 95 | 5 | 6 |
|  |  | 4.0 | 0.5 | 95 | 5 | 6 |

Mass spectrometry conditions
MS data were acquired in continuum mode and operated in resolution mode;
LockSpray acquisition mode was real-time acquisition and no calibration was applied.

Calibration solution: real-time calibration (LockSpray) solution: 2 ng/μL LE solution;

Calibration solution for mass axis: 2 μg/μL sodium iodide solution.

Mass spectrometry parameters

| Intact protein molecular weight analysis | | | |
|---|---|---|---|
| Capillary voltage (V) | 3000 | Online desalting column acquisition time (min) | 0.4-4 |
| First-order cone voltage (V) | 35 | SEC column acquisition time (min) | 0-8 |
| Second-order cone voltage (V) | 4/0.1 (ADC sample) | Mass calibration range (m/z) | 100-3500 or above |
| Desolvation gas temperature (° C.) | 350 | Acquisition quality range (m/z) | 500-3500 or above |
| Desolvation gas flow (L/h) | 500 | Sampling time (sec) | 0.500 |
| Cone gas flow (L/h) | 50 | LockSpray scan time (sec) | 0.500 |
| ESI source temperature (° C.) | 130 | LockSpray scan interval (sec) | 30 |

Figure 3:
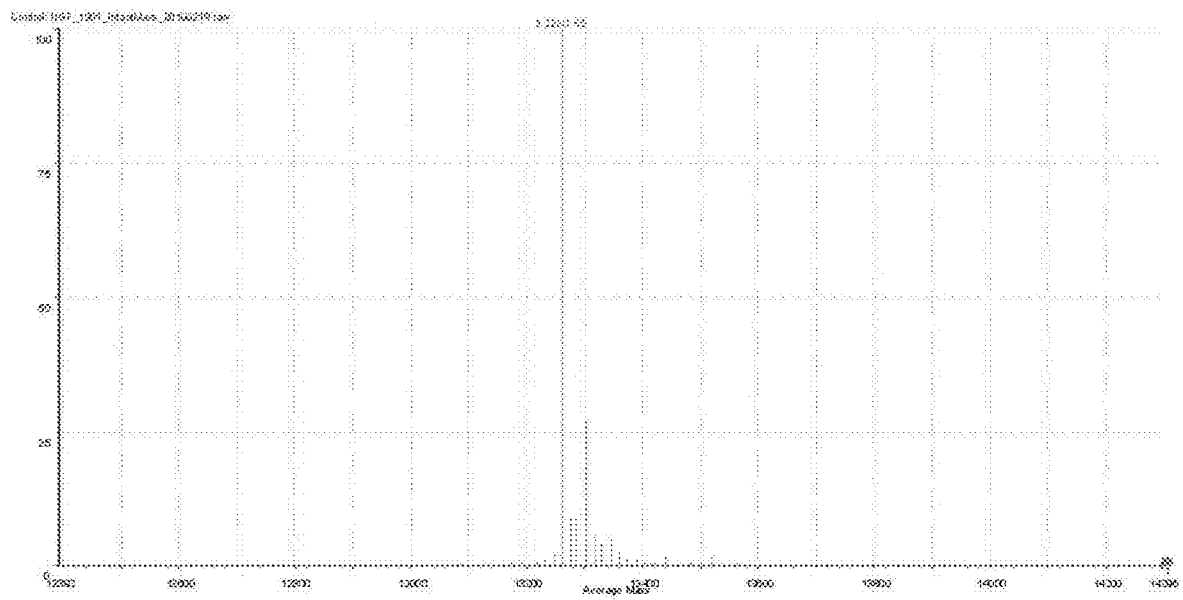
FIG. 3 is the mass spectrum of the target protein of the present invention, wherein the molecular weight of rhNGF is 13261.65.
Figure 4:
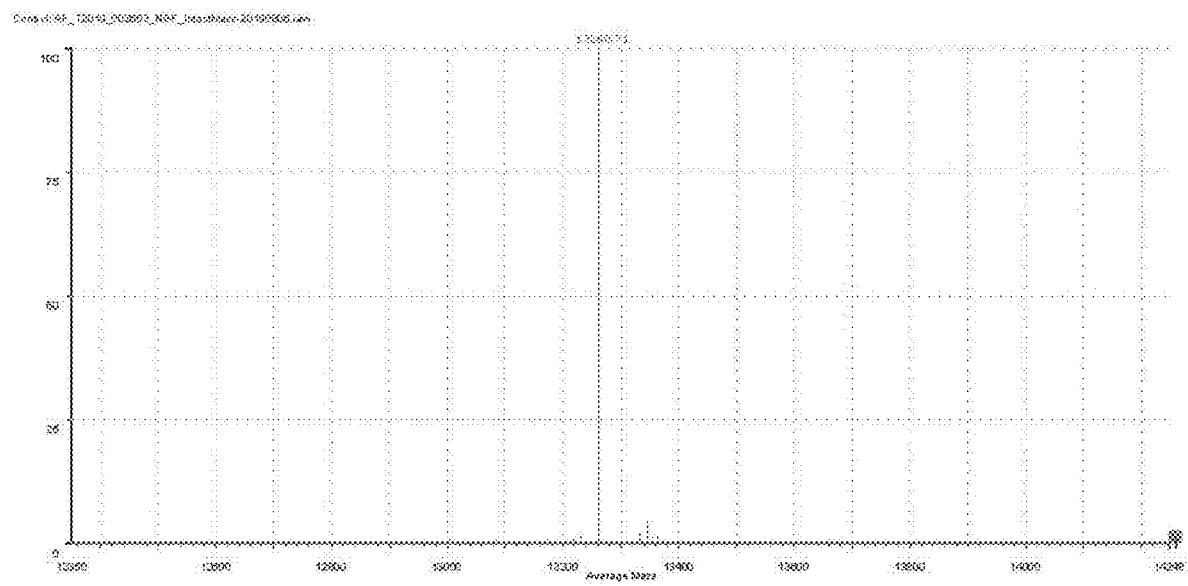
FIG. 4 is the mass spectrum of the target protein of the present invention, wherein the molecular weight of rhNGF is 13261.71.

The mass spectrum of the rhNGF prepared from the control sample using Tris buffer is shown in FIG. 3, in which there are many impurity peaks with molecular weights close to rhNGF. However, the mass spectrum of the rhNGF prepared using the $NH_4HCO_3$ buffer of the present invention is shown in FIG. 4, and there are almost no impurity peaks, the purity of the rhNGF sample is greatly improved.

Example 3: Determination of Biological Activity of the rhNGF

The biological activity of the rhNGF prepared in Example 2 and the commercial rhNGF (purchased from Sino Biological, Inc.) was determined by the TF1 cell proliferation method.

The experimental procedures are as follows:
1. TF1 cells (ATCC@CRL-2003™) in logarithmic growth phase were washed twice with pre-warmed 1640 medium (37° C.), and centrifuged at 300-500 g for 5 min;
2. TF1 cells were counted, suspended to an appropriate density with 1640 medium containing 10% FBS, and seeded into a 96-well plate, 10,000 cells/150 μL/well;
3. The rhNGF samples were diluted with 1640 medium in a 96-well plate into 9 gradients by three-fold serial dilution; the diluted samples were added to a 96-well cell culture plate, 50 μL/well; periphery of the 96-well plate was filled with 200 μL/well of distilled water;
4. The cells were incubated in an incubator at 37° C. and 5% $CO_2$ for 3 days (may be extended to 4 days if necessary);
5. After 3 days, 20 μL CCK-8 solution was added to each well of the 96-well cell culture plate, and cultured in a 37° C. incubator for another 8 hours;
6. After mixing, OD450 values were read using a microplate reader, data analysis and graphing were performed using GraphPad Prism6, and EC50 values were calculated.

Figure 5:
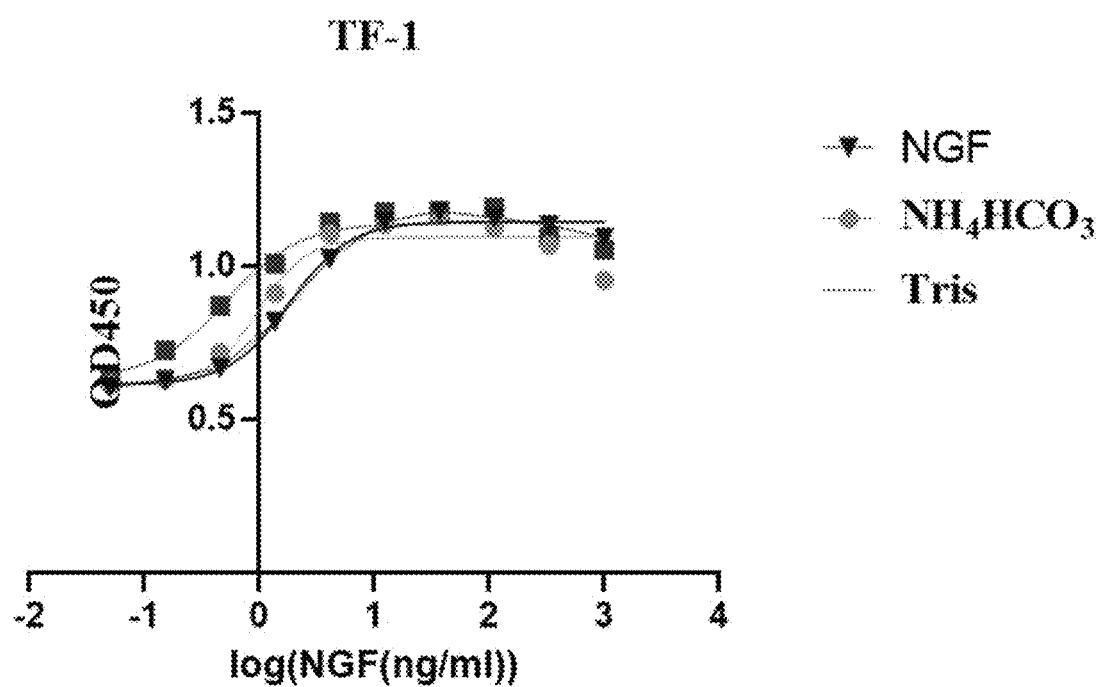
FIG. 5 is a graph showing that the target protein of the present invention promotes the proliferation of TF1 cells, wherein, NGF represents the profile of commercial rhNGF promoting TF1 cell growth, $NH_4HCO_3$ represents the profile of the rhNGF prepared by the method of the present invention promoting TF1 cell proliferation, and Tris represents the profile of rhNGF prepared in Tris buffer promoting TF1 cell proliferation.

The results are shown in FIG. 5. The rhNGF prepared using Tris buffer and the rhNGF prepared using ammonium bicarbonate buffer of the present invention can promote the proliferation of TF1 cells just like the commercial rhNGF, indicating that the rhNGF prepared by the method of the present invention has excellent biological activity, and can be used as a drug candidate.

What is claimed is:

1. A method for preparing a purified preparation of recombinant human nerve growth factor comprising:
   (a) expressing inclusion bodies of the recombinant human nerve growth factor in *E. coli*, and isolating the inclusion bodies from the *E. coli*;
   (b) washing the inclusion bodies with an inclusion body washing solution;
   (c) dissolving and denaturing the inclusion bodies by addition of a denaturing solution;
   (d) renaturing the denatured inclusion bodies by addition of a renaturing solution and a buffer; and
   (e) purifying the recombinant human nerve growth factor from the inclusion bodies;
   wherein ammonium bicarbonate is used as the buffer in the step (d).

2. The method of claim 1, wherein step (a) comprises the following steps:
   providing a nucleic acid encoding human nerve growth factor protein having an amino acid sequence as set forth in SEQ ID NO:1,
   whole gene synthesis of a human nerve growth factor gene,
   insertion of the human nerve growth factor gene into a vector,
   transformation of the vector into the *E. coli*,
   expression of the human nerve growth factor gene in the *E. coli*,
   disruption of the *E. coli* cells,
   centrifugation, and
   collection of precipitation or centrifugation pellet.

3. The method of claim 2, wherein:
   the vector is pET28a,
   the *E. coli* is *E. coli* expression strain BL21 (DE3) plyss,
   the expression is IPTG-induced expression, or
   the disruption is performed by sonication or homogenization.

4. The preparation method of claim 1, wherein:
   the step (b) comprises the following steps:
      subjecting the precipitation to resuspension in inclusion body washing solution A,
      sonication,
      centrifugation, and
      collection of precipitation,
   wherein the inclusion body washing solution A comprises 20-100 mM Tris, 50-150 mM NaCl, 1-10 mM EDTA, 0.5-3% Triton X-100, pH 8.0-8.5;
   subjecting the precipitation to resuspension in inclusion body washing solution B,
   sonication,
   centrifugation, and
   collection of precipitation,
   wherein the inclusion body washing solution B comprises 20-100 mM Tris, 50-150 mM NaCl, 1-10 mM EDTA, 1-4 M urea, pH 8.0-8.5;
   then subjecting the precipitation to resuspension in inclusion body washing solution C,
   sonication,
   centrifugation, and
   collection of precipitation,
   wherein the inclusion body washing solution C comprises 20-100 mM Tris, 50-150 mM NaCl, 1-10 mM EDTA, pH 8.0-8.5.

5. The method of claim 4, wherein: the step (b) comprises the following steps:
   subjecting the precipitation to resuspension in inclusion body washing solution A,
   sonication,
   centrifugation, and
   collection of precipitation,
   repeating the washing step once,
   wherein the inclusion body washing solution A comprises 50 mM Tris, 100 mM NaCl, 5 mM EDTA, 1% Triton X-100, pH 8.5;
   subjecting the precipitation to resuspension in inclusion body washing solution B, sonication, centrifugation, and
   collection of precipitation,
   repeating the washing step once,
   wherein the inclusion body washing solution B comprises 50 mM Tris, 100 mM NaCl, 5 mM EDTA, 2 M urea, pH 8.5;
   then subjecting the precipitation to resuspension in inclusion body washing solution C,
   sonication,
   centrifugation, and
   collection of precipitation, and
   repeating the washing step once, wherein the inclusion body washing solution C comprises 50 mM Tris, 100 mM NaCl, 5 mM EDTA, pH 8.5.

6. The method of claim 1, wherein: the step (c) comprises the following steps:
adding a denaturing solution to the inclusion bodies, wherein the denaturing solution comprises 8 M urea and 15-25 mM citric acid, pH 2.8-3.2, the denaturing solution being added according to a ratio of wet weight (g):volume (mL) 1:20-30 of the inclusion bodies and the denaturing solution, allowing the inclusion bodies to be dissolved, and
followed by centrifugation to remove the precipitation.

7. The method of claim 6, wherein: the denaturing solution comprises 8 M urea and 20 mM citric acid, pH 3.0, and the denaturing solution is added according to a ratio of wet weight (g):volume (mL) 1:25 of the inclusion bodies and the denaturing solution.

8. The method of claim 1, wherein: the step (d) comprises the following steps:
to the denaturing solution, adding a solution comprising: 0.8-1.0 M ammonium bicarbonate pH 8.0-9.0 and 8 M urea, and the amount of the added solution is one forth volume of the volume of the denaturing solution added,
adding DTT to a final concentration of 5-10 mM, maintaining at 25-37° C. for 30-60 min;
then adding oxidized glutathione to a final concentration of 20-40 mM,
maintaining at 25-37° C. for 10-15 min;
then adding 19 volumes of dilution buffer, the dilution buffer comprising 50-150 mM Na$_2$HPO$_4$, 5-15 mM ethanolamine, 4.2-4.6 M urea, 14-18% PEG300, pH 8.3-8.5;
then adding cysteine to a final concentration of 1-5 mM;
subjecting the mixture to deaeration with argon and renaturation at 4° C. for 1-7 days; and
subjecting the renaturing solution to ultrafiltration concentration with a 3K membrane to a final concentration of rhNGF of 1-2 mg/mL.

9. The method of claim 8, wherein:
the concentration of ammonium bicarbonate is about 1 M, pH is 8.5,
the final concentration of DTT is about 5 mM,
the final concentration of oxidized glutathione is about 20 mM, and
the dilution buffer comprises about 100 mM Na$_2$HPO$_4$, about 10 mM ethanolamine, about 4.6 M urea, about 15.8% PEG300, about pH 8.3, and the final concentration of cysteine is about 3 mM.

10. The method of claim 1, wherein: the step (e) comprises the steps of SP purification and C4 reversed-phase chromatography.

11. The method of claim 1, wherein: the preparation method comprises the following steps:

1) expressing the inclusion bodies of recombinant human nerve growth factor in *E. coli*, and isolating the inclusion bodies from the *E. coli*,
wherein the human nerve growth factor has an amino acid sequence as set forth in SEQ ID NO: 1, the vector is pET28a, the *E. coli* is *E. coli* expression strain BL21 (DE3) plyss, and the expression is IPTG-induced expression;
2) washing the inclusion bodies of the step 1) with inclusion body washing solutions, respectively, wherein:
2a) washing the inclusion bodies with inclusion body washing solution A, which comprises about 50 mM Tris, about 100 mM NaCl, about 5 mM EDTA, about 1% Triton X-100, and about pH 8.5;
2b) washing the inclusion bodies obtained in the step 2a) with inclusion body washing solution B, which comprises about 50 mM Tris, about 100 mM NaCl, about 5 mM EDTA, about 2 M urea, about pH 8.5;
2c) washing the inclusion bodies obtained in the step 2b) with inclusion body washing solution C, which comprises 50 mM Tris, 100 mM NaCl, 5 mM EDTA, pH 8.5;
3) dissolving the inclusion bodies obtained in the step 2) by addition of a denaturing solution,
wherein the denaturing solution comprises about 8 M urea and about 20 mM citric acid, about pH 3.0, and the denaturing solution is added according to a ratio of wet weight (g):volume (mL) 1:25 of the inclusion bodies and the denaturing solution;
4) renaturing the inclusion bodies obtained in the step 3): to the denaturing solution of the step 3) by adding a solution comprising: about 1.0 M, about pH 8.5 ammonium bicarbonate, and about 8 M urea, and the amount of the added solution is one forth volume of the volume of the denaturing solution added,
adding DTT to a final concentration of 5 mM,
maintaining at between about 25-37° C. for 30-60 min;
then adding oxidized glutathione to a final concentration of 20 mM,
maintaining at between about 25-37° C. for 10-15 min;
then adding 19 volumes of dilution buffer,
wherein the dilution buffer comprises about 100 mM Na$_2$HPO$_4$, about 10 mM ethanolamine, about 4.6 M urea, about 15.8% polyethylene glycol 300 (PEG300), about pH 8.3; then adding cysteine to a final concentration of about 3 mM;
subjecting the mixture to deaeration with argon and renaturation at about 4° C. for 1-7 days; and
subjecting the renaturing solution to ultrafiltration concentration with a 3K membrane to a final concentration of rhNGF of about 1-2 mg/mL.

12. The method of claim 11, further comprising repeating steps 2a) to 2c) before step 3.

* * * * *